(12) United States Patent
Pellerin

(10) Patent No.: US 6,726,899 B2
(45) Date of Patent: *Apr. 27, 2004

(54) CALCIFIED TISSUE FACING PREPARATION CONTAINING ANTIMICROBIAL AGENT

(75) Inventor: Joseph J. Pellerin, Clarkston, MI (US)

(73) Assignee: Advantage Dental Products, Inc., Lake Orion, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/277,534

(22) Filed: Oct. 22, 2002

(65) Prior Publication Data

US 2003/0072781 A1 Apr. 17, 2003

Related U.S. Application Data

(63) Continuation-in-part of application No. 09/806,041, filed as application No. PCT/US99/21265 on Sep. 23, 1999, now Pat. No. 6,494,717.
(60) Provisional application No. 60/101,655, filed on Sep. 24, 1998.

(51) Int. Cl.$^7$ ................................................. A61K 6/08
(52) U.S. Cl. .................. 424/54; 433/217.1; 433/217.2; 106/35; 523/115; 523/116; 514/634; 514/635
(58) Field of Search .................. 424/54; 433/217.1, 433/217.2; 106/35; 523/116, 115; 514/634, 635

(56) References Cited

U.S. PATENT DOCUMENTS

| | | | |
|---|---|---|---|
| 3,925,543 A | 12/1975 | Donohue | 424/52 |
| 3,934,002 A | 1/1976 | Haefele | 424/54 |
| 4,883,534 A | 11/1989 | Sandham et al. | 106/35 |
| 5,068,107 A | 11/1991 | Hollibush et al. | 424/435 |
| 5,133,957 A | 7/1992 | Suh et al. | 424/49 |
| 5,178,870 A | 1/1993 | Schaeken | 424/405 |
| 5,180,577 A | 1/1993 | Polefka et al. | 424/52 |
| 5,213,615 A | 5/1993 | Michl | 106/35 |
| 5,270,351 A | 12/1993 | Bowen | 523/116 |
| 5,304,369 A | 4/1994 | Rheinberger et al. | 424/52 |
| 5,330,746 A | 7/1994 | Friedman | 424/49 |
| 5,340,581 A | 8/1994 | Tseng et al. | 424/401 |
| 5,393,516 A | 2/1995 | Rheinberger et al. | 424/52 |
| 5,401,783 A | 3/1995 | Bowen | 523/116 |
| 5,575,652 A | 11/1996 | Gaffar et al. | 433/173 |
| 5,622,552 A | 4/1997 | Arnold | 106/35 |
| 5,708,052 A | 1/1998 | Fischer et al. | 106/35 |
| 5,738,113 A | 4/1998 | Connelly | 128/898 |
| 5,851,551 A | 12/1998 | Tseng et al. | 424/486 |
| 5,866,630 A | 2/1999 | Mitra et al. | 523/118 |
| 5,876,208 A | 3/1999 | Mitra et al. | 433/217.1 |
| 5,888,491 A | 3/1999 | Mitra et al. | 523/109 |
| 5,945,087 A | 8/1999 | Nelson et al. | 424/49 |
| 6,093,084 A | 7/2000 | Jeffries | 451/37 |
| 6,136,885 A | 10/2000 | Rusin et al. | 523/116 |
| 6,312,668 B2 | 11/2001 | Mitra et al. | 424/49 |
| 6,326,417 B1 | 12/2001 | Jia | 523/116 |

FOREIGN PATENT DOCUMENTS

WO   WO 89/10736   11/1989

*Primary Examiner*—Frederick Krass
(74) *Attorney, Agent, or Firm*—Gifford, Krass, Groh, Sprinkle, Anderson & Gitkowski, P.C.

(57) ABSTRACT

The present invention provides a calcified tissue facing preparation characterized by having a polymerizable resin, and an antimicrobial agent of the formula:

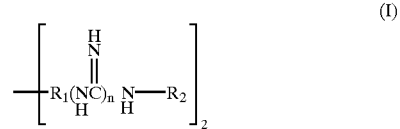

where $R_1$ is a hydrocarbon radical having between 1 and 16 carbon atoms, n is an integer between 1 and 8 inclusive and X is a halogen atom selected from fluorine, chlorine or bromine. It is appreciated that $R_1$ includes unsaturated hydrocarbon radicals, as well as heteroatom containing radicals. Preferably, the molecule of Formula (I) is associated with an adduct species. At least one of glutaraldehyde or a chelating agent are added to enhance the preparation characteristics.

30 Claims, No Drawings

CALCIFIED TISSUE FACING PREPARATION CONTAINING ANTIMICROBIAL AGENT

RELATED APPLICATIONS

This application is a continuation-in-part of U.S. patent application Ser. No. 09/806,041 filed Mar. 26, 2001, now U.S. Pat. No. 6,494,717 which claims priority of PCT Application Serial No. PCT/US99/21265 filed Sep. 23, 1999, which claims the benefit of U.S. Provisional Patent Application Serial No. 60/101,655 filed Sep. 24, 1998, which are incorporated herein by reference.

FIELD OF THE INVENTION

This invention relates to compositions for sealing calcified tissue substrates to inhibit infection and promote subsequent restorative material bonding; in particular, the invention is tailored to dentinal tubules, in order to prevent dentinal hypersensitivity and further to promote effective bonding of subsequent restorative dental materials such as amalgams, composites, resins and cementitious materials.

BACKGROUND OF THE INVENTION

Dental caries are a common disease of modem humankind. The treatment of dental caries involves the removal of the carious lesion by a number of means including mechanical drilling and light ablation. The ensuing removal of dentin brings the dental nerve endings contained within the pulp into proximity with the mouth. Filling the resulting cavity in order to isolate the nerve endings leaves the tooth susceptible to thermal hypersensitivity via thermal conduction through the filling as well as bacterial infection. Bacterial colonization of the filled cavity induces further caries formation and hypersensitivity.

Currently, polymeric resinous materials are widely used to fill cavities, as well as in cosmetic dentistry and corrective dental structures including brackets, braces, veneers, onlays, crowns, and the like. In adhering dental structures to tooth enamel, there are minor problems with thermal or bacterial hypersensitivity.

In contrast, when the dentin of a tooth is exposed as a result of cervical erosion or tooth decay, changes occur in the physical structure of the dentin. Whereas tooth enamel is a densified, nonporous substance, dentin is characterized by a porous structure containing thousands of dentinal tubules. The dentinal tubules extend outward from the tooth pulp and terminate at or before the tooth enamel. These tubules contain pressurized pulp fluid which seeps from the pulp when the ends of the tubules are exposed. Collagen fibers are also associated with the tubules.

Typically, neither cervical erosion nor drilling of dentin directly exposes the ends of the dental tubules. Cervical erosion surfaces are characterized by irregularities and hemispherical protrusions. The dentinal tubules are mostly filled with inorganic material although some maintain openings of various sizes. Drilling of dentin creates a debris field which is characterized by weakened and cracked dentin. Since the debris field is structurally unsound, adhering a restorative material thereto creates a weak filling.

The cleaning of dentin prior to bonding a material thereto is thus highly advantageous. Typically, acid etching is used to decalcify the surface dentin and enlarge the openings of the tubules. Acid etching leaves behind the protruding collagen fibers that are associated with the dentinal tubes. Chelating agents such as EDTA are known to help dissolve calcified deposits associated with a dentinal tubule opening. These collagen fibers represent a substrate for bacterial colonization as well as a hydrophilic surface for the bonding of a polymeric resinous material. The acid etching solution is typically a 20–50% by weight solution of phosphoric acid, but also includes citric and nitric acids.

A number of facing preparations are currently in use to seal and disinfect a dentin surface following acid etching. These preparations typically include a monomeric resin capable of cross linking to the collagen fibers. Glutaraldehyde (GLUMA, Heraeus Kulzer, Inc.) and benzalkonium chloride (Healthdent, Inc.) are added as antimicrobials. These prior art antimicrobials are limited in their efficacy. Glutaraldehyde polymerizes in water and thereby the effective dosages decrease. Furthermore, glutaraldehyde is a known irritant as well as antiseptic and thereby may induce the dental hypersensitivity which the facing preparation is designed to prevent. Benzalkonium chloride is a potent antimicrobial yet is incompatible with anionic detergents such as soap, as well as with nitrates. While the benzalkonium cation is electrically attracted to dentin, stearic considerations prevent optimal interactions between the radical and dentinal tubules.

SUMMARY OF THE INVENTION

The present invention provides a facing preparation composition containing a polymerizable resin and an antimicrobial agent having the formula:

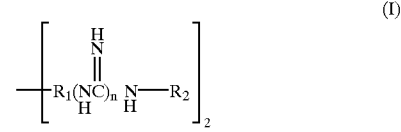

where $R_1$ is a hydrocarbon having between 1 and 16 carbon atoms, n is an integer between 1 and 8 inclusive, $R_2$ is selected from the group consisting of halophenyl and 2-ethylhexyl. The antimicrobial agent is delivered in the form of an organic salt, with the anionic species illustratively selected from: acetate, gluconate, propionate, and acrylate. Optionally, a solvent is also provided to promote diffusion of the other composition components into a substrate. Solvents operative in the present invention illustratively include: methanol, water, acetone, methyl ethyl ketone, and isopropanol.

The facing preparation composition also includes 0.1 to 20% by weight glutaraldehyde as a secondary and synergistically acting antimicrobial. Alternatively, a chelating agent is present in the facing preparation in order to complex calcified deposits associated with dentinal tubule openings so as to prepare a clean dentinal tubule bonding surface.

An antimicrobial oral rinse contains the antimicrobial agent present at greater than 0.2% by weight in a buccal cavity compatible solvent containing a chelating agent and excluding the polymerizable resin of the facing preparation composition.

DETAILED DESCRIPTION OF THE INVENTION

The present invention pertains to compositions for facing and disinfecting a calcified tissue structure. The facing preparation of the present invention inhibits thermal and microbial hypersensitivity in proximal nerves of the organism. The facing preparation of the present invention also promotes bonding of a subsequent structural sealing layer to the calcified tissue. The term "calcified tissue" as used herein is defined to mean periosteum, cortical bone, tooth enamel, cementum, dentin, and pulp. The present invention has particular utility in facing and disinfecting exposed dentin for subsequent bonding of additional restorative dental materials.

Optionally, calcified tissue substrates are etched by means conventional to the art, prior to application of a facing preparation of the instant invention. Acid etching generally involves application of mineral acids illustratively including phosphoric, nitric, citric and hydrofluoric acids. It is appreciated that mechanical etching using an abrasive grit is also operative herein. Following etching, extraneous acid and debris are removed from the substrate by irrigating the etched substrate with water. The substrate is then blotted or evaporatively dried by means illustratively including an air jet.

The facing preparation of the instant invention contains a polymerizable resin. The term "polymerizable resin" as defined herein means either a hydrophilic polymerizable compound having at least one hydroxyl moiety therein, a hydrophobic polymerizable hydrocarbon, or a polymerizable compound having both a hydrophobic and a hydrophilic moiety therein. Polymerizable resins operative within the present invention illustratively include hydroxyalkyl methacrylates, hydroxyalkyl acrylates, alkyl methacrylates, alkyl acrylates, polyhydric alcohols, mixtures thereof, substituted derivatives thereof and the like. Specific polymerizable resins operative within the present invention illustratively include 2-hydroxymethyl methacrylate (HMMA), 2-hydroxyethyl methacrylate (HEMA), bisphenol-A-glycidyl methacrylate prepolymer (bis-GMA), N-phenylglycine/glycidyl methacrylate (NPG-GMA), bis(glycerol dimethacrylate) phosphate, glycerol methacrylate, methyl acrylate, triethylene glycol dimethacrylate and the like. Preferably, hydrophilic resins such as HMMA and HEMA are used in facing preparations of the present invention which are tailored to treatment of inherently moist substrates, such as dentin. The facing preparations of the present invention preferably include a polymerizable resin present in amounts ranging from about 10–90% by weight relative to the total facing preparation weight. More preferably, the polymerizable resin is included in the facing preparation in amounts from 20–60 weight percent relative to the total facing preparation weight. Most preferably, the polymerizable resin is included in the facing preparation in amounts from 30–50 weight percent relative to the total facing preparation weight.

The facing preparation of the present invention optionally further includes a solvent. The solvent promoting diffusion of the facing preparation into microscopic pores and crevices of the substrate. The solvent is chosen to impart solubility on the polymerizable resin used in a particular facing preparation. In those instances where the osteoporotic substrate is dentin, hydrophilic solvents are preferred. Solvents operative within a facing preparation of the present invention illustratively include: ethanol, water, acetone, methyl ethyl ketone, and isopropanol. The solvent is preferably present in the facing preparation in amounts ranging from 10–90% relative to the total facing preparation weight. More preferably, the solvent is included in the facing preparation in an amount ranging from 20–80% by weight relative to the total facing preparation weight. Most preferably, the solvent is included in the facing preparation in an amount ranging from 30–70% by weight relative to the total facing preparation weight. It is appreciated that a miscible mixture of solvents is also operative herein.

The facing preparation of the present invention also includes an antimicrobial agent of the formula:

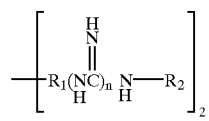

where $R_1$ is a hydrocarbon radical having between 1 and 16 carbon atoms, n is an integer between 1 and 8 inclusive and $R_2$ is selected from halophenyl and 2-ethylhexyl. It is appreciated that $R_1$ includes unsaturated hydrocarbon radicals, as well as heteroatom containing radicals. Preferably, the molecule of Formula (I) is associated with an adduct species. The adduct species being selected to promote solubility in the facing preparation. Adduct species operative in the present invention illustratively include: acetate, gluconate, propionate, and acrylate. Preferably, $R_1$ is a saturated hydrocarbon. Preferably, $R_1$ has between 1 and 6 carbon atoms. Preferably, the halophenyl is chlorophenyl. More preferably, the halophenyl is para-halophenyl. Specific antimicrobial agents of Formula (I) illustratively include: alexidine, chlorhexidine, alexidine gluconate, chlorhexidine gluconate, alexidine acetate, chlorhexidine acetate and chlorhexidine digluconate.

Both alexidine and chlorhexidine are effective antimicrobials against a wide range of vegative gram positive and gram negative organisms. The facing preparation of the present invention is preferably buffered to pHs ranging from about 5–9. More preferably, the present invention is buffered to pHs ranging from 6–9.

The antimicrobial agent of Formula (I) is present in an inventive facing formulation between 0.1 and 10% by weight. Preferably, the antimicrobial agent (I) is present from 0.2 to 5% by weight.

A synergistic effect is noted in the present invention based on the dual action of an antimicrobial agent of Formula (I) in combination with glutaraldehyde. While the specific mechanism remains unclear, a cumulative improvement is observed in facing properties upon consideration of the properties of bond strength, tissue irritation, and restoration sensitivity. Typically, glutaraldehyde is present at 0.1 to 20% by weight and at a ratio of between 1:5 and 5:1 relative to the antimicrobial agent of Formula (I) subject to the quantity of glutaraldehyde present. Preferably, the glutaraldehyde to antimicrobial agent of Formula (I) ratio is between 1:3 and 3:1. Still more preferably, the antimicrobial agent of Formula (I) is present at between 1 and 5% by weight. In a most preferred embodiment, the antimicrobial agent of Formula (I) is present at 3% by weight and glutaraldehyde is present at 1 to 5% by weight, with a 1:1 ratio therebetween being highly effective.

Optionally, an additive biocide is introduced into the compositions of the present invention. Benzalkonium chloride is operative as an additive in the present invention compositions between 0.1 and 10% by weight of the total composition weights. It is appreciated that other additives, adjuvants, surfactants, stabilizers, dyes, and emulsifiers are also added optionally to the present invention. In particular, fluoride solution present to about 0.5% by weight is a well established wash effective against dental caries.

In an alternate embodiment of the present invention, a chelating agent is introduced into an inventive facing preparation, independent of the presence of glutaraldehyde therein. The chelating agent is dissolved in the inventive facing preparation and is capable of complexing those ions which are present in a calcified deposit associated with a dentinal tubule opening.

Suitable chelating agents useful in the present invention illustratively include ethylenediaminetetraacetic acid (EDTA), diethylenetriaminepentaacetic acid (DTPA), nitrilotriacetic acid (NTA), iminodiacetic acid (IDA), iminotriacetic acid (ITA), ethylenediamine (En), N,N'-diethylenediamine (Den), diethylenetriamine (DTN), diethylenetetramine (Trien), triaminotriethylene amine, propylenediamine, glycolic acid, hydroxybutyric acid, salicylic acid, benzoic acid, mixtures thereof and other polydentate chelating agents which are compatible with the buccal cavity and active in binding divalent cations such as $Ca^{2+}$, $Mg^{2+}$, $Fe^{2+}$, and the like. Binding of calcium ions a preferred function of a chelating agent according to the present invention. Preferably, the chelating agent of the present invention contains carboxylate moieties. More preferably, the chelating agent is EDTA. A chelating agent of the present invention is dissolved in an inventive facing preparation in an amount of about 3% by total weight to solution saturation at 20° C. Chelating agent solutions are typically between 3% and 20% by weight of the facing preparation. Preferably, the chelating agent is present between 7% and 18% by total weight; more preferably, at between 9% and 14% by total weight.

It is appreciated that an acid is optionally introduced to modify the buffered pH of the facing preparation and modify the chelation characteristics of the inventive preparation. Suitable pH lowering acids useful in the present invention illustratively include ascorbic, acetic, propionic, formic, succinic, hydrochloric, sulfuric, nitric, phosphoric, orthophosphoric and citric.

In another embodiment, solutions of the antimicrobial agent (I) are provided which lack the polymerizable resin. This solution has utility as an oral rinse to cleanse the buccal cavity and in particular tubules prior to application of conventional dental structures. While such rinses have previously been utilized having between about 0.12% to 0.20% chlorohexidine, considerably more effective antimicrobial formulations are disclosed herein. An antimicrobial rinse according to the present invention includes between 0.2 and 10% by weight of antimicrobial based on total solution weight. Preferably, the rinse contains 0.2 to 5% antimicrobial. More preferably, the rinse contains a solvent of water, acetone or ethanol or mixtures thereof.

It is appreciated that the facing preparation of the present invention may also include other conventional microbial agents which have a complementary antimicrobial spectrum to those of Formula (I). The microbial agents of Formula (I) are particularly effective over time owing to charge interactions between the substrate and the agents of Formula (I).

The following examples are given for the purpose of illustrating various embodiments of the invention and are not meant to limit the present invention in any way.

EXAMPLE 1

A dentin facing preparation is formed from the following components:

| Component | % by Weight of the Total Preparation |
|---|---|
| HEMA | 45 |
| Ethanol | 50 |
| Chlorhexidine | 5 |

Dentin is etched with a 40% phosphoric acid solution. The etched dentin is irrigated with water and dried with an air jet. The facing preparation is mixed and swabbed onto the dentin surface and allowed to air dry for about 20 seconds. The facing preparation is overlayered with a HEMA based polymerizable sealant Prodigy with Optibond Solo (Kerr Corp.). A strong filling persisted for greater than 6 months. The patient experienced no hypersensitivity associated with exposing the filled dentin cavity to hot water, bite pressure, or ice. The process is repeated and found to be repeatable with comparable sealant strengths.

EXAMPLE 2

A dentin facing preparation is formed of the following components:

| Component | % by Weight of the Total Preparation |
|---|---|
| HMMA | 40 |
| Water | 59 |
| Chlorhexidine gluconate | 1 |

This facing preparation composition behaves similarly to the composition of the primer in Example 1.

EXAMPLE 3

A dentin facing preparation is formed from the following components:

| Component | % by Weight of the Total Preparation |
|---|---|
| HEMA | 50 |
| Ethanol | 30 |
| Water | 10 |
| Chlorhexidine acetate hydrate | 10 |

This facing preparation composition behaves similarly to the composition of the facing preparation in Example 1.

EXAMPLE 4

A dentin facing preparation is formed from the following components:

| Component | % by Weight of the Total Preparation |
|---|---|
| HEMA | 40 |
| Water | 50 |
| Alexidine gluconate | 5 |
| Benzalkonium chloride | 5 |

This facing preparation composition behaves similarly to the composition of the facing preparation in Example 1.

EXAMPLE 5

A cementum facing preparation is formed from the following components:

| Component | % by Weight of the Total Preparation |
|---|---|
| Glycerol methacrylate | 28 |
| Ethanol | 18 |

-continued

| Component | % by Weight of the Total Preparation |
|---|---|
| Water | 48 |
| Chlorhexidine gluconate | 6 |

The facing preparation prevented cervical infection and afforded good bond strength when a subsequent bis-GMA sealant resin is applied.

EXAMPLE 6

A cortical bone facing preparation is formed from the following components:

| Component | % by Weight of the Total Preparation |
|---|---|
| HMMA | 55 |
| Water | 41 |
| Chlorhexidine | 3 |
| Ciprofloxin | 1 |

The facing preparation promoted adhesion to a cyanomethacrylate based bonding material.

EXAMPLE 7

The in vitro tensile bond strength of a conventional tooth bonding composite Prodigy with Optibond Solo (Kerr Corp.) is measured with and without the dentin facing preparation of Example 1. Bond strength and failure modes are determined for bonding to superficial and deep dentin sites.

| Bond Strength, MPa | | |
|---|---|---|
| | Superficial Dentin | Deep Dentin |
| Control | 27 ± 13 | 28 ± 8 |
| With facing preparation of Example 1 | 36 ± 11 | 29 ± 6 |

| Failure Sites, % | | |
|---|---|---|
| | Superficial Dentin | Deep Dentin |
| Control | 54A/46C | 44A/26C/30T |
| With facing preparation of Example 1 | 22A/68C/10T | 46A/48C/6T | where A is an adhesive failure at the tooth-composite surface, C is cohesive failure in the composite and T is a cohesive failure in the dentin.

EXAMPLE 8

Standardized cultures of Strept. mutans are grown in petri dishes and subjected to 30 second submersion in 20 milliliters of various concentration rinses of aqueous chlorhexidine. A 0.04% chlorhexidine solution and water serve as controls. Thereafter, the petri dishes are incubated and colony members counted after 48 hours.

| Chlorhexidine Concentration (wt. %) | Colony Member After Rinse |
|---|---|
| 0 | 196 |
| 0.04 | 26 |
| 0.2 | 0 |
| 0.5 | 1 |
| 1.0 | 1 |
| 2.0 | 0 |
| 5.0 | 2 |
| 10.0 | 0 |

EXAMPLE 9

A dentin facing preparation is formed from the following components:

| Component | % by Weight of the Total Preparation |
|---|---|
| HEMA | 45 |
| Ethanol | 49 |
| Chlorhexidine gluconate | 3 |
| Glutaraldehyde | 3 |

The procedure of Example 1 was followed with comparable results except bond strengths were higher relative to the preparation of Example 1.

EXAMPLE 10

A dental facing preparation is formed of the following components:

| Component | % by Weight of the Total Preparation |
|---|---|
| HMMA | 40 |
| Water | 47 |
| EDTA | 10 |
| Chlorhexidine acetate hydrate | 3 |

This facing preparation behaved similarly to the composition provided in Example 2 except with higher bond strengths.

Those skilled in the art will readily appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon considering the specification and following claims.

What is claimed is:
1. A facing preparation composition comprising:
   a polymerizable acrylate resin;
   0.1 to 10 weight percent, based on the weight of the composition, of an antimicrobial agent having the formula:

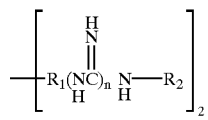

where $R_1$ is a hydrocarbon having between 1 and 16 carbon atoms, n is an integer between 1 and 8 inclusive, $R_2$ is selected from the group consisting of halophenyl and 2-ethylhexyl, said antimicrobial agent being coupled to a solubility promoter; and 0.1 to 20% by weight based on the weight of the composition, of glutaraldehyde.

2. The facing preparation composition of claim 1 wherein said antimicrobial agent is chlorhexidine.

3. The facing preparation composition of claim 1 wherein said antimicrobial agent is alexidine.

4. The facing preparation composition of claim 1 wherein said solubility promoter is selected from the group consisting of: acetate, gluconate, propionate, and acrylate.

5. The facing preparation composition of claim 1 wherein said antimicrobial agent is present from 1 to 5 weight percent.

6. The facing preparation composition of claim 1 wherein glutaraldehyde is present from 1 to 5% by weight.

7. The facing preparation composition of claim 5 wherein glutaraldehyde is present in an amount of less than 20 weight percent and the weight ratio between said antimicrobial agent and glutaraldehyde is between 1:5 and 5:1.

8. The facing preparation composition of claim 1 further comprising a chelating agent.

9. The facing preparation composition of claim 8 wherein said chelating agent is present between 3 and 20% by weight, based on the weight of the composition.

10. The facing preparation composition of claim 8 wherein said chelating agent is selected from the group consisting of: ethylenediaminetetraacetic acid, diethylenetriaminepentaacetic acid, nitrilotriacetic acid, iminodiacetic acid, iminotriacetic acid, ethylenediamine, N,N'-diethylenediamine, diethylenetriamine, diethylenetetramine, triaminotriethylene amine, propylenediamine, glycolic acid, hydroxybutyric acid, salicylic acid, benzoic acid, and mixtures thereof.

11. The facing preparation composition of claim 8 wherein said chelating agent is ethylenediaminetetraacetic acid.

12. A facing preparation composition comprising:

a polymerizable acrylate resin;

0.1 to 10% by weight, based on the weight of the composition of an antimicrobial agent having the formula:

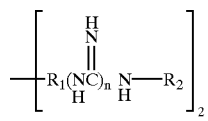

where $R_1$ is a hydrocarbon having between 1 and 16 carbon atoms, n is an integer between 1 and 8 inclusive, $R_2$ is selected from the group consisting of halophenyl and 2-ethylhexyl, said antimicrobial agent being coupled to a solubility promoter; and a chelating agent capable of complexing ions present in a calcified deposit associated with a dental surface.

13. The facing preparation composition of claim 12 wherein said antimicrobial agent is chlorhexidine.

14. The facing preparation composition of claim 12 wherein said antimicrobial agent is alexidine.

15. The facing preparation composition of claim 12 wherein said solubility promoter is selected from the group consisting of: acetate, gluconate, propionate, and acrylate.

16. The facing preparation composition of claim 12 wherein said antimicrobial agent is present from 1 to 5 weight percent.

17. The facing preparation composition of claim 12 comprising a chelating agent, said agent optionally containing carboxylate moieties.

18. The facing preparation composition of claim 17 wherein said chelating agent is present between 3 and 20% by weight, based on the weight of the composition.

19. The facing preparation composition of claim 17 wherein said chelating agent is selected from the group consisting of: ethylenediaminetetraacetic acid, diethylenetriaminepentaacetic acid, nitrilotriacetic acid, iminodiacetic acid, iminotriacetic acid, ethylenediamine, N,N'-diethylenediamine, diethylenetriamine, diethylenetetramine, triaminotriethylene amine, propylenediamine, glycolic acid, hydroxybutyric acid, salicylic acid, benzoic acid, and mixtures thereof.

20. The facing preparation composition of claim 12 further comprising 0.1 to 20% by weight glutaraldehyde, based on the weight of the composition.

21. The facing preparation composition of claim 12 wherein said chelating agent is present from 9 to 14 weight percent, based on the weight of the composition.

22. The facing preparation composition of claim 12 further comprising a solvent selected from the group consisting of: water, ethanol, acetone, and mixtures thereof.

23. The facing preparation composition of claim 12 further comprising a pH lowering acid.

24. A commercial package comprising a composition of 1) a composition comprising a polymerizable acrylate resin, an antimicrobial agent of Formula (I) according to claim 1 and at least one component selected from the group consisting of: glutaraldehyde and a chelating agent and 2) labeling having printed instructions indicating the use thereof as a dental facing preparation.

25. A process for cleansing a dentin tubule prior to application of a dental structure, the process comprising the steps of:

(a) swabbing a tooth surface with an antimicrobial mixture, the mixture comprising at least 0.2% by weight, based on the weight of the composition, of an antimicrobial agent having the formula:

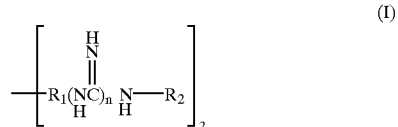

where $R_1$ is a hydrocarbon having between 1 and 16 carbon atoms, n is an integer between 1 and 8 inclusive, $R_2$ is selected from the group consisting of halophenyl and 2-ethylhexyl, and a buccal cavity compatible solvent, and 3 to 20 percent by weight, based on the weight of the composition of a chelating agent; and (b) applying the dental structure.

26. The process of claim 25 wherein said antimicrobial agent is present from 0.2 to 5% by weight.

27. The process of claim 25 wherein said antimicrobial agent of Formula (I) is coupled to a solubility promoter selected from the group consisting of: acetate, gluconate, propionate, and acrylate.

28. The process of claim 25 wherein said chelating agent is selected from the group consisting of: ethylenediaminetetraacetic acid, diethylenetriaminepentaacetic acid, nitrilotriacetic acid, iminodiacetic acid, iminotriacetic acid, ethylenediamine, N,N'-diethylenediamine, diethylenetriamine, diethylenetetramine, triaminotriethylene amine, propylenediamine, glycolic acid, hydroxybutyric acid, salicylic acid, benzoic acid, and mixtures thereof.

29. The process of claim 26 wherein said chelating agent is ethylenediaminetetraacetic acid.

30. A process for preparing a tooth for a dental procedure comprising the steps of:

(a) priming a tooth for application of a dental facing composition;

(b) providing the dental facing composition wherein the composition comprises a polymerizable acrylate resin, from 0.1 to 10 weight percent, based on the weight of the composition, of an antimicrobial agent having the formula:

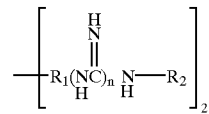

where $R_1$ is a hydrocarbon having between 1 and 16 carbon atoms, n is an integer between 1 and 8 inclusive, $R_2$ is selected from the group consisting of halophenyl and 2-ethylhexyl, said antimicrobial agent being coupled to a solubility promoter, and at least one of: 0.1 to 10 weight percent glutaraldehyde or from 3 to 20 weight percent, based on the weight of the composition, of a chelating agent; and (c) applying the dental facing composition to the tooth surface, wherein the application of the dental facing composition prepares the tooth for the dental procedure.

* * * * *

UNITED STATES PATENT AND TRADEMARK OFFICE
CERTIFICATE OF CORRECTION

PATENT NO. : 6,726,899 B2
DATED : April 27, 2004
INVENTOR(S) : Pelerin

It is certified that error appears in the above-identified patent and that said Letters Patent is hereby corrected as shown below:

<u>Title page,</u>
Item [75], Inventors, "Pellerin" should be replaced with -- Pelerin --.

Signed and Sealed this

Sixth Day of September, 2005

JON W. DUDAS
*Director of the United States Patent and Trademark Office*